United States Patent
Studer et al.

(10) Patent No.: US 6,447,543 B1
(45) Date of Patent: Sep. 10, 2002

(54) BASKET-LIKE CONTAINER FOR IMPLANTING BONE TISSUE

(75) Inventors: Armin Studer, Steinhausen; Thomas Bollinger, Urdorf, both of (CH)

(73) Assignee: Sulzer Orthopedics Ltd., Baar (CH)

(*) Notice: Subject to any disclaimer, the term of this patent is extended or adjusted under 35 U.S.C. 154(b) by 0 days.

(21) Appl. No.: 09/625,596

(22) Filed: Jul. 26, 2000

(30) Foreign Application Priority Data

Sep. 28, 1999 (EP) .............................................. 99810873

(51) Int. Cl.$^7$ .................................................. A61F 2/44
(52) U.S. Cl. .................................. 623/17.11; 623/17.15
(58) Field of Search ........................... 623/17.11, 17.12, 623/17.16, 23.53, 23.54

(56) References Cited

U.S. PATENT DOCUMENTS

| | | | |
|---|---|---|---|
| 4,064,567 A | * 12/1977 | Burstein et al. | ............... 3/1.91 |
| 5,026,373 A | * 6/1991 | Ray et al. | ..................... 606/61 |
| 5,397,359 A | * 3/1995 | Mittelmeier et al. | ........ 623/16 |
| 5,443,510 A | * 8/1995 | Shetty et al. | .................. 419/2 |
| 6,086,613 A | * 7/2000 | Camino et al. | ............... 623/17 |

FOREIGN PATENT DOCUMENTS

| | | |
|---|---|---|
| EP | 0268115 A1 | 5/1988 |
| FR | 2726994 | 5/1996 |
| WO | WO 94/18913 | 9/1994 |
| WO | WO 97/23175 | 7/1997 |
| WO | WO 98/26725 | 6/1998 |
| WO | WO 99/32055 | 7/1999 |

* cited by examiner

Primary Examiner—Corrine McDermott
Assistant Examiner—Hieu Phan
(74) Attorney, Agent, or Firm—William Micheal Hynes; Townsend and Townsend and Crew, LLP

(57) ABSTRACT

The basket-like container (1) contains a reception volume for bone tissue. After the filling in of the bone tissue the container is implanted. The reception volume is located within a wall (2) which is arranged about an axis (10). This peripheral wall consists of a grid, a fabric or a mesh. Transversely to the axis the wall enables an X-ray optical seeing through of the unfilled reception volume. The surface component, which is permeable by X-rays, amounts to at least 30%.

9 Claims, 3 Drawing Sheets

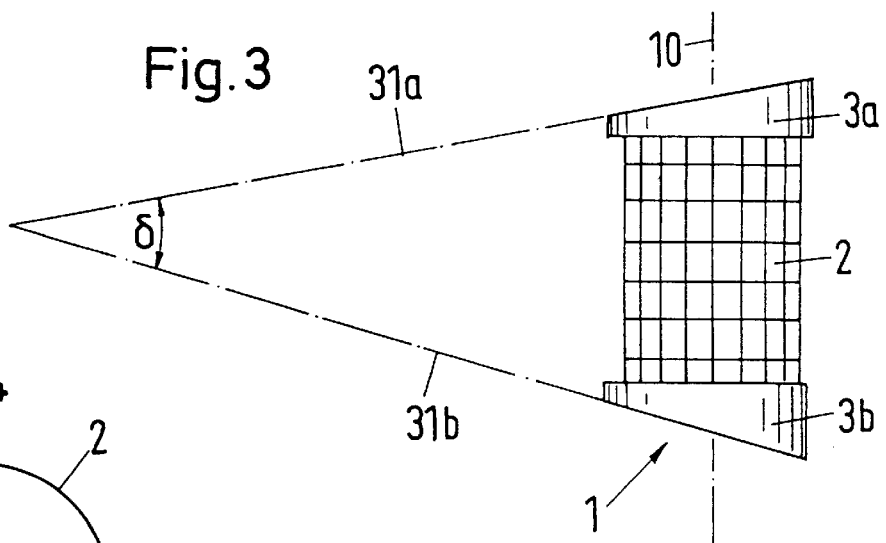
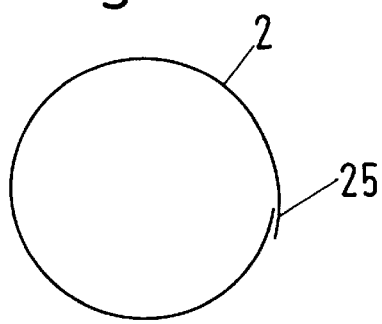
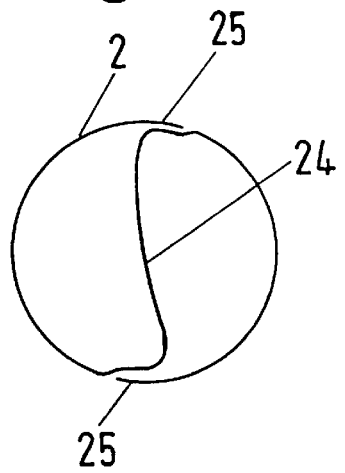
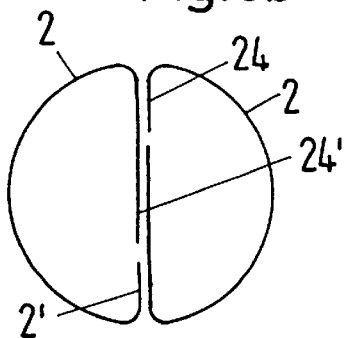
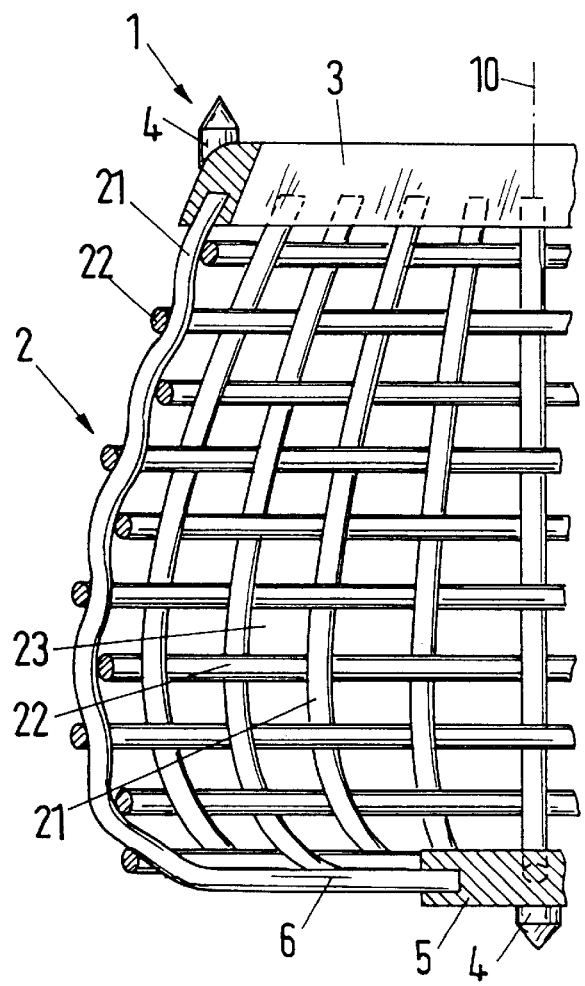

BASKET-LIKE CONTAINER FOR IMPLANTING BONE TISSUE

BACKGROUND OF THE INVENTION

The invention relates to a basket-like container for implanting bone tissue.

It is known to perform surgical interventions at spinal columns in order to replace defective intervertebral discs by implants. Adjacent vertebrae are stiffly connected with implants of this kind, which form the distance maintaining elements between vertebrae. It is also known to remove bone tissue from a patient in order to implant the former at a different location for reconstruction purposes, where this tissue grows together to a stiff body thanks to its regenerative force. In spinal columns it is advantageous when the named distance maintaining elements are at least partly produced with bone tissue, with it being possible for its regenerative forces to be of use.

SUMMARY OF THE INVENTION

The object of the invention is to create an implant by means of which bone tissue of a patient can be implanted in or between bones of the patient. In addition a diagnosis method must be realizable by means of which a progress of a bone tissue formation can be checked. This object is satisfied by a basket-like container for the reception of bone tissue designed for subsequent implantation to the body. The basket-like container defines a reception volume for bone tissue which is located within a wall which is arranged about an axis. This peripheral wall consists of a grid, which is a fabric or a mesh. The grid is selected to enable an X-ray optical seeing through of the unfilled reception volume transversely to the axis which amounts to at least 30%.

The basket-like container contains a reception volume for bone tissue. After a filling in of the bone tissue the container is implanted.

The reception volume is located within a wall which is arranged about an axis. This peripheral wall consists of a grid, a fabric or a mesh. Transversely to the axis the wall enables an X-ray optical seeing through of the unfilled reception volume. The surface component, which is permeable by X-rays, amounts to at least 30%.

Various constructions are disclosed for the container. In a first embodiment, the wall is built up of wires, which are crossed at binding points, with the wires of a first array being oriented largely parallel to the axis of the container. The remaining wires form a second array, being directed transversely to the first array. All the wires together provide a support function so that dense packing of bone tissue can occur into the reception volume. It is disclosed that the wires parallel to the axis can have a larger diameter than remaining wires. Furthermore, the wall of the container can be arranged to be seamless. The container can be provided with a base, which is transverse to the axis.

The central portion of the container can include a reinforcement wall connecting the peripheral wall in a reinforcing manner. Preferred construction of the grid includes titanium. Absorbable material can be incorporated to the wall. Furthermore the wall can be bounded by a ring. This ring can be placed at an edge, which extends transversely to the axis. Anchoring tips can be preferably arranged on the ring.

A method of use of the container is disclosed. The container can be used for surgical intervention at spinal columns. An intervertebral disc can be substituted by at least one container—and preferably two containers. The container(s) produce a stiffening and distance maintaining connection between vertebrae of the spinal columns. Further, the container can be anchored to removed bone tissue by substituting at least part of the bone tissue filled container to the spatial interval from which bone tissue has been removed.

BRIEF DESCRIPTION OF THE DRAWINGS

FIG. 3 is a second embodiment of the container in accordance with the invention, FIG. 4 is a schematic cross-sectional illustration of a container wall, FIGS. 5a, 5b are corresponding cross-sections of two-chambered containers, FIG. 6 is a further embodiment of the container in accordance with the invention.

DESCRIPTION OF THE PREFERRED EMBODIMENTS

Figure 1:
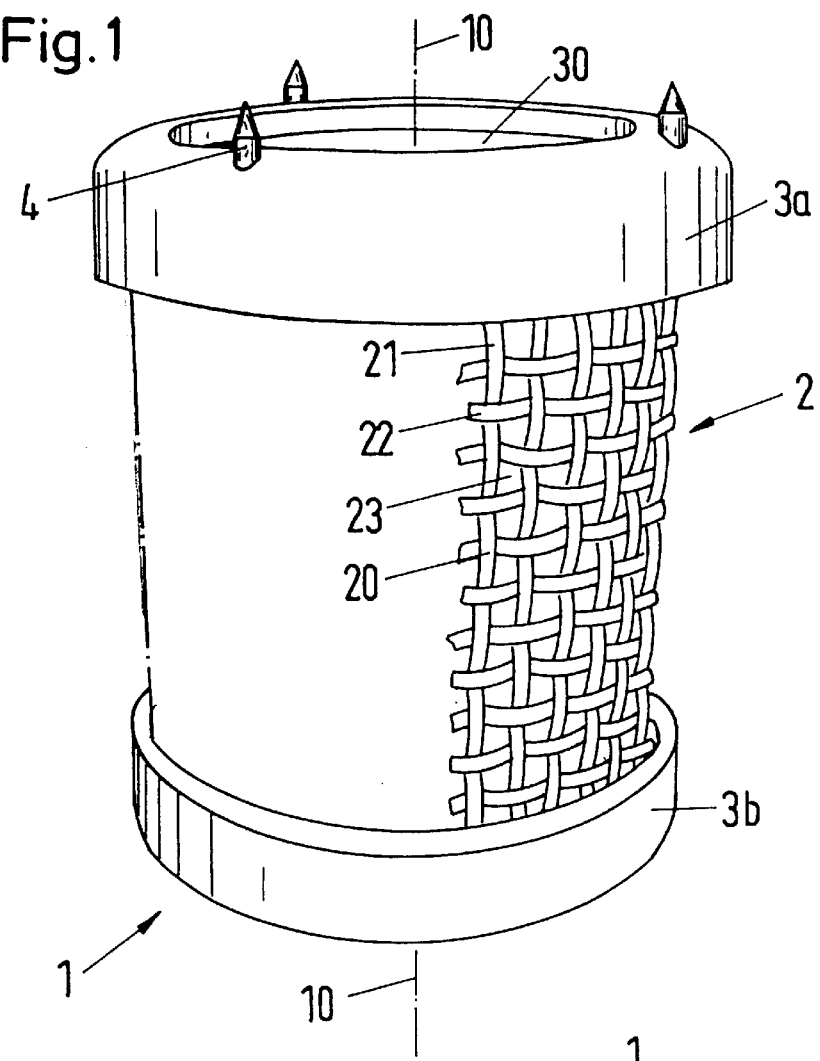
FIG. 1 is a perspective illustration of a container in accordance with the invention.

A container 1 in accordance with the invention, as is illustrated in perspective in FIG. 1, is implanted as a stiffening and distance maintaining element between vertebrae in a surgical intervention which is performed on the spinal column of a patient. Prior to the implantation the basket-like container 1 is filled with bone tissue which had been taken from the patient at a different location. The reception volume for the bone tissue is located within a wall 2 which is arranged about an axis 10. This peripheral wall 2—in the form of a grid, fabric or mesh is for example built up of wires 21, 22 which are crossed at binding points 20. The wires 21 of a first array are oriented to be parallel to the axis; the remaining wires 22, which form a second array, are oriented to be transverse to the first array. Relatively large openings 23 are provided between the wires 21, 22. They enable an X-ray optical seeing through of the unfilled reception volume transversely to the axis 10 which amounts to at least 30% in accordance with the invention. The compound of all wires 21, 22 is intended to provide a sufficient support function so that—in order to be able to produce a dense packing—the bone tissue can be pressed in into the reception volume.

The X-ray optical seeing through enables the regenerative progress of the tissue which is contained in the container 1 to be monitored in check-up examinations after an implantation.

The wall 2 is bounded by rings 3a and 3b at an edge which extends transversely to the axis 10. Tips 4 are arranged on these rings which enable an anchoring in the vertebrae to be treated during the implantation. The upper ring 3a contains an opening 30, through which the bone tissue can be filled in into the reception volume. The lower ring 3b can also have a corresponding opening. The container 1 however advantageously has at the lower ring 3b a base, which can be formed of the same wire structure as the wall 2.

Figure 2:
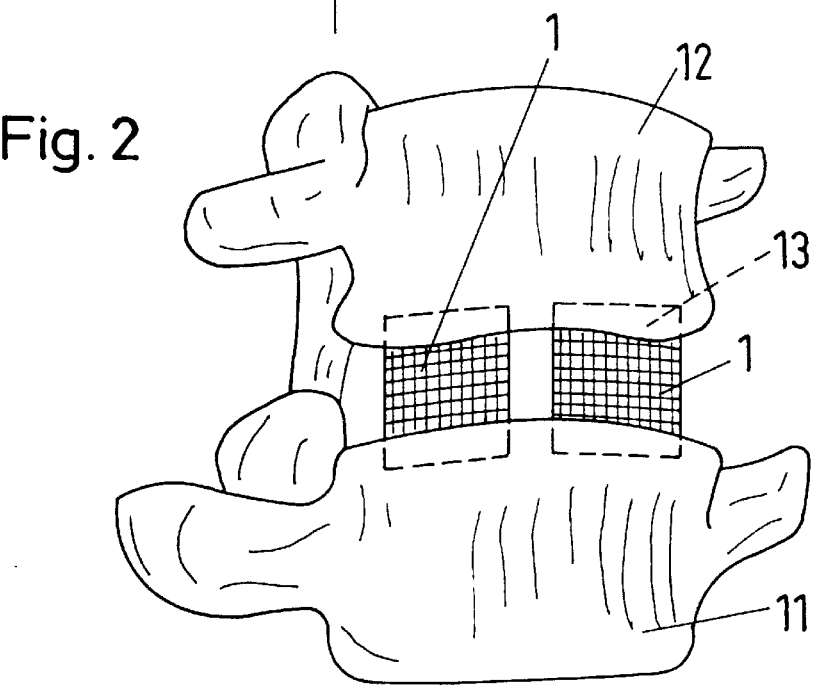
FIG. 2 shows two vertebrae of a spinal column with containers in accordance with the invention arranged between them.

FIG. 2 shows a first lumbar vertebra 11 of a spinal column which is connected via two containers 1 in accordance with the invention to a second lumbar vertebra 12. Bone tissue can be removed at the vertebrae 11 and 12 in order to form depressions 13 for the containers 1.

The rings 3a and 3b, which are arranged parallel to one another in the embodiment in accordance with FIG. 1, can also be designed as is illustrated in FIG. 3, namely in such a manner that the outer sides of the rings 3a and 3b which are transverse to the axis 10 lie on planes 31a and 31b which enclose an angle 6. Containers 1 in accordance with FIG. 3 can be used in surgical treatments of lordosis in the region of the lumbar vertebral column.

The wall 2 can—see FIG. 4—be simply produced from a flat wire mesh in that this mesh is formed to a cylinder and an overlapping strip is welded to form a seam 25. In the embodiment of FIG. 5a a flat wire mesh is formed in such a manner that two chambers and two seams 25 are formed. An inner wall 24 acts as a reinforcement of the peripheral wall 2. Another two-chambered embodiment is illustrated in FIG. 5b. Here two tube pieces 2' and 2" are fitted together along a planar wall 24'.

The containers 1 in accordance with the invention can also be offered as longer tubes, the walls 2 of which are formed in such a manner that they can be cut to a required length. In this the rings 3a and 3b and the wall 2 are provided as separate parts which can be fitted together after the cutting to length of the wall 2.

In the embodiment in accordance with FIGS. 4, 5a and 5b the walls 2 are produced from flat mesh pieces. It is however also possible to form the wall 2 as a spatial interlacing. An example is illustrated in FIG. 6 as the left half of a longitudinal section through the container 1. Vertical wires 21 connect in an arcuate manner an upwardly lying entrance ring 3 to a disc 5 which is arranged at the base 6 of the container 1 and thereby form a wall 2 which widens downwardly to a part of the base 6. Wires 22 are woven in transversely to the wires 21. The wires 22 can be closed rings with different diameters; but they can also form a connected piece, however, which is woven in helically between the wires 21. Anchoring tips 4 are attached at the entrance ring 3 and at the base disc 5. The openings 23 are formed to be so large that the X-ray optical seeing through in accordance with the invention transversely to the axis 10 is possible.

Figure 7:
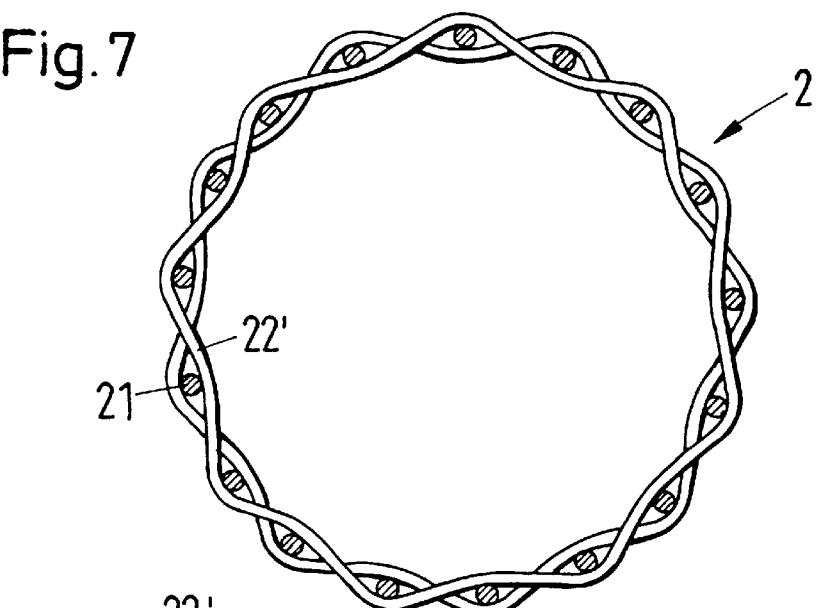
FIG. 7 is a cross-section through a seamless container wall.
Figure 8:
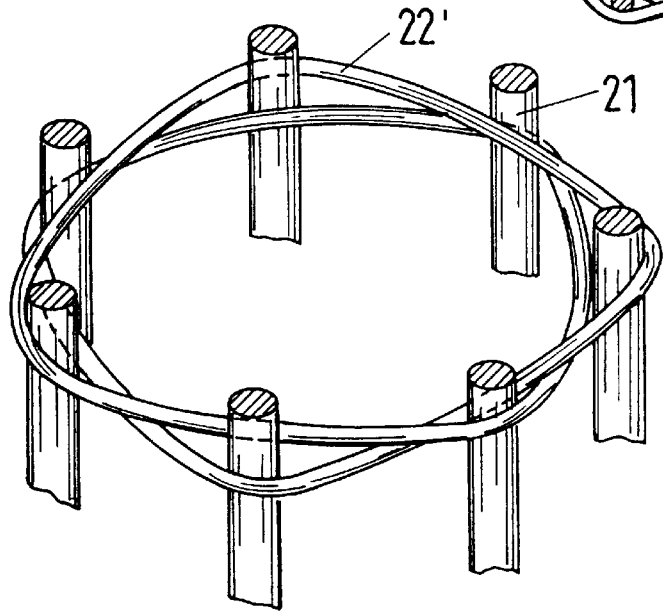
FIG. 8 is an oblique view for illustrating the construction of the seamless container wall and FIG. 9 is a side view of a container wall with the construction in accordance with FIG. 8.
Figure 9:
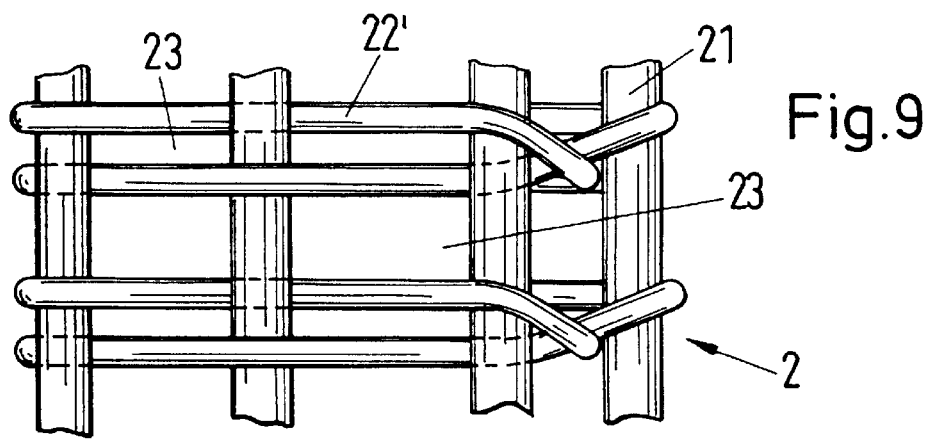

The container 1 of FIG. 6 has a seamless wall 2. A further example of a seamless wall 2 is shown in FIG. 7. The wires 22' which are woven in between seventeen (uneven number) vertical wires 21 form double rings, as is illustrated in FIG. 8 for an embodiment with only seven vertical wires 21. In order that such a seamless embodiment is possible, the number of vertical wires 21 must be uneven. With reference to the side view in FIG. 9 with two double rings 22' it is illustrated that the openings 23 in the wall 2 can be formed to have different sizes.

The wires 21 of the first array have a larger diameter than the other wires 22 in order that they—in a compounding with the wires of the second array—can withstand a larger force in the direction of the axis 10. Suitable metals, in particular titanium, or suitable alloys can be used as the material for all implants. A portion of the walls 2, which is for example formed by some of the wires 22, can also be non metallic and for example consist of absorbable material.

The cross-section of the container 1 in accordance with the invention need not necessarily be circular. The wall 2 can for example have the shape of a square or a hexagon.

In addition to the treatment of spinal columns the container in accordance with the invention—if suitably shaped—can be used for a surgical intervention at the bone in order to substitute for tissue which had to be removed for example as a result of a cancerous tumor.

What is claimed is:

1. A basket-like container for the reception of bone tissue and for subsequent implantation to a body comprising:
   a wall (2), arranged about an axis (10), consisting of a wire grid;
   the wall (2) built up of wires (21, 22) in first and second arrays crossed at binding points (20);
   the wires (21) of the first array being oriented largely parallel to the axis (10);
   the wires (22) of the second array being directed transversely to the wires of the first array;
   the resultant wire grid providing a reception volume with a sufficient support function to enable dense packing of bone tissue pressed into the reception volume defined by the container; and,
   the grid enabling an x-ray optical seeing through of at least 30% of an unfilled reception volume transversely to the axis (10) of the container.

2. The basket-like container for the/reception of bone tissue and for subsequent implantation to the body according to claim 1 and wherein:
   the wires (21) of the first array have a larger diameter than the wires (22) of the second array whereby the wires of the first array can withstand a predetermined force in the direction of the axis (10) of the container.

3. The basket-like container for the reception of bone tissue and for subsequent implantation to the body according to claim 1 and wherein:
   the wall (2) is seamless.

4. The basket-like container for the reception of bone tissue and for subsequent implantation to the body according to claim 1 and wherein:
   the wall (2) has a reception volume with a base (6) transverse to the axis (10) of the basket-like container.

5. The basket-like container for the reception of bone tissue and for subsequent implantation to the body according to claim 1 and wherein:
   a reinforcement wall (24, 24') is disposed within the reception body for reinforcement of the wall (2).

6. The basket-like container for the reception of bone tissue and for subsequent implantation to the body according to claim 1 and wherein:
   the wires (21, 22) include titanium.

7. The basket-like container for the reception of bone tissue and for subsequent implantation to the body according to claim 1 and including:
   a ring (3, 3a, 3b) at least at an edge of the wall (2), the ring extending transversely to the axis (10); and,
   anchoring tips (4) arranged on the rings for fastening to the wall (2).

8. A method of using a basket-like container for the reception of bone tissue and for subsequent implantation to the body comprising the steps of providing
   providing at least one basket-like container including,
   a wall (2), arranged about an axis (10), consisting of a wire grid;
   the wall (2) built up of wires (21, 22) in first and second arrays crossed at binding points (20);
   the wires (21) of the first array being oriented largely parallel to the axis (10);

the wires (22) of the second array being directed transversely to the wires of the first array;

the resultant wire grid providing a reception volume with a sufficient support function to enable dense packing of bone tissue pressed into the reception volume defined by the container; and, the grid enabling an x-ray optical seeing through of at least 30% of an unfilled reception volume transversely to the axis (10) of the container, filling the basket-like container with bone tissue;

implanting the basket-like container between vertebrae of the spinal column to produce a stiffening and distance maintaining connection between vertebrae; and, monitoring the unfilled reception volume by x-ray optical seeing through of the container.

9. The method of using a basket-like container for the reception of bone tissue and for subsequent implantation to the body according to claim 8 and wherein the implanting step includes:

removing tissue from the spinal column to define an insertion interval in the spinal column; and, placing the basket-like container into the insertion interval.

\* \* \* \* \*